(12) United States Patent
Dilek Hacihabiboglu et al.

(10) Patent No.: US 12,195,440 B2
(45) Date of Patent: Jan. 14, 2025

(54) HIGH YIELD, ECO-FRIENDLY RECYCLING METHOD OF POLYLACTIC ACID USING SUPERCRITICAL OR DENSE GAS CARBON DIOXIDE

(71) Applicant: ORTA DOGU TEKNIK UNIVERSITESI, Ankara (AR)

(72) Inventors: Cerag Dilek Hacihabiboglu, Ankara (AR); Naime Asli Sezgi, Ankara (AR); Seda Sivri, Ankara (AR)

(73) Assignee: ORTA DOGU TEKNIK UNIVERSITESI, Ankara (TR)

( * ) Notice: Subject to any disclaimer, the term of this patent is extended or adjusted under 35 U.S.C. 154(b) by 662 days.

(21) Appl. No.: 17/621,705

(22) PCT Filed: Mar. 30, 2020

(86) PCT No.: PCT/TR2020/050252
§ 371 (c)(1),
(2) Date: Dec. 22, 2021

(87) PCT Pub. No.: WO2020/263201
PCT Pub. Date: Dec. 30, 2020

(65) Prior Publication Data
US 2022/0267292 A1 Aug. 25, 2022

(30) Foreign Application Priority Data
Jun. 26, 2019 (TR) .................... 2019/09479

(51) Int. Cl.
*C07D 319/12* (2006.01)

(52) U.S. Cl.
CPC .................... *C07D 319/12* (2013.01)

(58) Field of Classification Search
CPC ........................................ C07D 319/12
USPC .......................................... 549/274
See application file for complete search history.

(56) References Cited

U.S. PATENT DOCUMENTS 10,457,661 B2 * 10/2019 Ito .................... C08J 11/16
2019/0001669 A1    1/2019 Kawatoko et al.

FOREIGN PATENT DOCUMENTS

| CN | 109293623 A   | 2/2019  |
|----|---------------|---------|
| JP | 4171823 B2    | 10/2008 |
| JP | 2019031684 A  | 2/2019  |
| WO | 2015112098 A1 | 7/2015  |

OTHER PUBLICATIONS

Roeb Garcia-Arrazola, et al., Lipase-catalyzed synthesis of poly-l-lactide using supercritical carbon dioxide, The Journal of Supercritical Fluids, 2009, pp. 197-201, 51(2).

* cited by examiner

*Primary Examiner* — Kristin A Vajda
(74) *Attorney, Agent, or Firm* — Bayramoglu Law Offices LLC

(57) ABSTRACT

A recycling method of polylactic acid in a single step by using supercritical or dense gas carbon dioxide is provided. The recycling method includes the steps of adjusting a temperature of a reactor to at least 120° C., and adjusting a pressure to values above or below a critical pressure of carbon dioxide, wherein the critical pressure is 73.8 bar.

13 Claims, 2 Drawing Sheets

HIGH YIELD, ECO-FRIENDLY RECYCLING METHOD OF POLYLACTIC ACID USING SUPERCRITICAL OR DENSE GAS CARBON DIOXIDE

CROSS REFERENCE TO THE RELATED APPLICATIONS

This application is the national stage entry of International Application No. PCT/TR2020/050252, filed on Mar. 30, 2020, which is based upon and claims priority to Turkish Patent Application No. 2019/09479 filed on Jun. 26, 2019, the entire contents of which are incorporated herein by reference.

TECHNICAL FIELD

The invention is related to the recycling method of polylactic acid to valuable chemicals such as lactide in a single step by using supercritical or dense gas carbon dioxide.

BACKGROUND

The problem of environmental pollution caused by plastic waste has led to increasing interest in biodegradable plastics. Polylactic acid (PLA) has started to replace commercial polymers that are frequently used in applications other than the biomedical industry, due to the preferable thermal, mechanical, and barrier properties that they exhibit.

While the demand for PLA leads to an increase in production capacity and reduction in costs, it also shows that PLA waste shall increase due to its common usage. Moreover, due to low number of microorganism types that enable biological degradation of PLA, the absence of these microorganisms in most kinds of soil, the necessity of the required conditions for the biological degradation, and the slow degradation rate, it is anticipated that biodegradation shall not be sufficient for recycling of PLA.

Polylactic acid is a biodegradable polymer that is produced from lactic acid, which can be obtained from resources with high content of starch such as corn, sugar, and flour.

To produce polylactic acid, first lactic acid needs to be converted into lactide by means of dimerization and following this, polylactic acid is synthesized from lactide by means of ring-opening polymerization. However, in the production process of polylactic acid from lactic acid, the conversion step of lactic acid to lactide step is fairly costly.

Due to this reason in recent years, studies have been conducted on conversion of polylactic acid to lactide with depolymerization of polylactic acid and conversion of lactide to polylactic acid by means of ring-opening polymerization.

The patent document numbered CN109293623A is related to the production of lactide by recycling of polylactic acid with a depolymerization reaction. However, in this patent document, the mentioned depolymerization process is a multi-step process. Moreover, catalysts are used during depolymerization and depolymerization is not carried out in a supercritical or dense gas $CO_2$ medium. As the process comprises the use of the catalyst, the separation process of lactide from the catalyst extends the recycling period.

The patent document numbered US 2019/0016696A1 is similarly related to the production of lactide by recycling of polylactic acid with depolymerization reaction. The lactide product is collected as gas from the extruder, subjected to a purification process, and liquified by cooling. However, in this patent document, the PLA recycling process and the lactide formation are multi-step processes, and a catalyst is required to breakdown the polymer in the depolymerization reaction that is carried out in the extruder.

The patent document numbered WO 2015/112098 A1 is related to a process for producing lactide by preparation of PLA-based small-sized plastics, converting PLA into low molecular weight PLA in the range of 500-30,000 g/mol by means of alcoholysis and hydrolysis, and following this, subjecting the PLA to thermal decomposition. In the alcoholysis reaction, where high-molecular weight PLA is converted into low-molecular weight PLA, an alcohol and a catalyst, or in the hydrolysis reaction, which is suggested as an alternative, water and a catalyst are used. Following this process, a catalyst is used for lactide production by means of thermal decomposition of the produced low-molecular weight PLA.

To summarize, organic solvents and water are used in the recycling methods of polylactic acid in the prior art. Due to this reason, the product requires a separation process. This situation does not only increase the costs of the techniques substantially, but it also has negative effects on the environment due to the volatile organic components that are emitted by the organic solvents and due to the fact that separation processes cannot be performed with high efficiency.

According to the above-mentioned information, design of an alternative environmentally benign process is necessary for PLA recycling, which provides high yield of lactide production, does not use any organic solvent and water, eliminating the separation process cost and waste.

SUMMARY

The present invention is related to high yield, eco-friendly recycling method of polylactic acid using supercritical or dense gas carbon dioxide, which provides the above-mentioned requirements, eliminates the disadvantages of the prior art of the techniques, and has further advantages.

The prior aim of the invention is recycling of polylactic acid using supercritical or dense gas carbon dioxide.

Another aim of the invention is to convert polylactic acid to lactide with high purity (≥94%).

While the final product of some of the known recycling techniques of PLA is lactic acid, with this invention, the final product of the PLA recycling with supercritical or dense gas carbon dioxide is lactide. In the case of the lactide that is produced with the invention being used in PLA production, it is possible to produce PLA by eliminating the necessity of the conversion step of lactic acid and methyl lactate to lactide.

With the invention, the organic solvent, water, and/or catalyst that are used in the prior art of the technique, are not used in PLA depolymerization. Thereby low cost, highly pure, environmentally friendly products that do not require a separation process are obtained by using only supercritical or dense gas carbon dioxide.

With the invention, as supercritical or dense gas $CO_2$ is used instead of organic solvents or water, the volatile organic compounds emitted by organic solvents are eliminated and the industrial utilization of water is prevented.

Another important advantage of using supercritical or dense gas $CO_2$ is that the product can easily be separated from $CO_2$. This easy separation process is enabled by reducing the pressure of the system to atmospheric pressure.

As a result, in reaction or material processing, the costly and energy consuming separation processes are not required for the removal of $CO_2$.

The other important advantage of using supercritical $CO_2$ is that in the supercritical phase, $CO_2$ has a density that is close to the liquid density and transport properties such as viscosity and diffusion coefficient close to those of gas. Besides these features, it exhibits specific intermolecular interactions due to its quadruple moment. All these features facilitate the mass transfer of $CO_2$ into the material and ensure the reaction to be carried out at lower temperatures and in shorter periods of time.

By means of the invention, an environmentally friendly system has been designed which does not produce waste, does not cause emission of organic volatile compounds and prevents water pollution with industrial usage.

BRIEF DESCRIPTION OF THE DRAWINGS

The figures prepared for the detailed description of the high yield, eco-friendly recycling method of polylactic acid by using supercritical or dense gas carbon dioxide have been given below.

DEFINITIONS OF THE PARTS/ASPECTS/SECTIONS FORMING THE INVENTION

The parts and sections provided in the figures that have been prepared for the detailed description of the high yield, eco-friendly recycling method of polylactic acid by using supercritical or dense gas carbon dioxide have each been numbered, and the description of each number has been given below.

T1: Liquid Carbon Dioxide Tank
V1: Liquid Carbon Dioxide Tank Outlet Valve
V2: Syringe Pump Inlet Valve
P1: Syringe Pump
V3: Syringe Pump Outlet Valve
V4: Reactor Inlet Valve
R1: Reactor
K1: Thermocouple and Temperature Controller
K2: Reactor Mixer
G1: Pressure Transducer and Display
D1: Rupture Disk
V5: Reactor Outlet Valve
H1: Ventilation System
1: Polylactic acid
2: Lactide

DETAILED DESCRIPTION OF THE EMBODIMENTS

Figure 1:
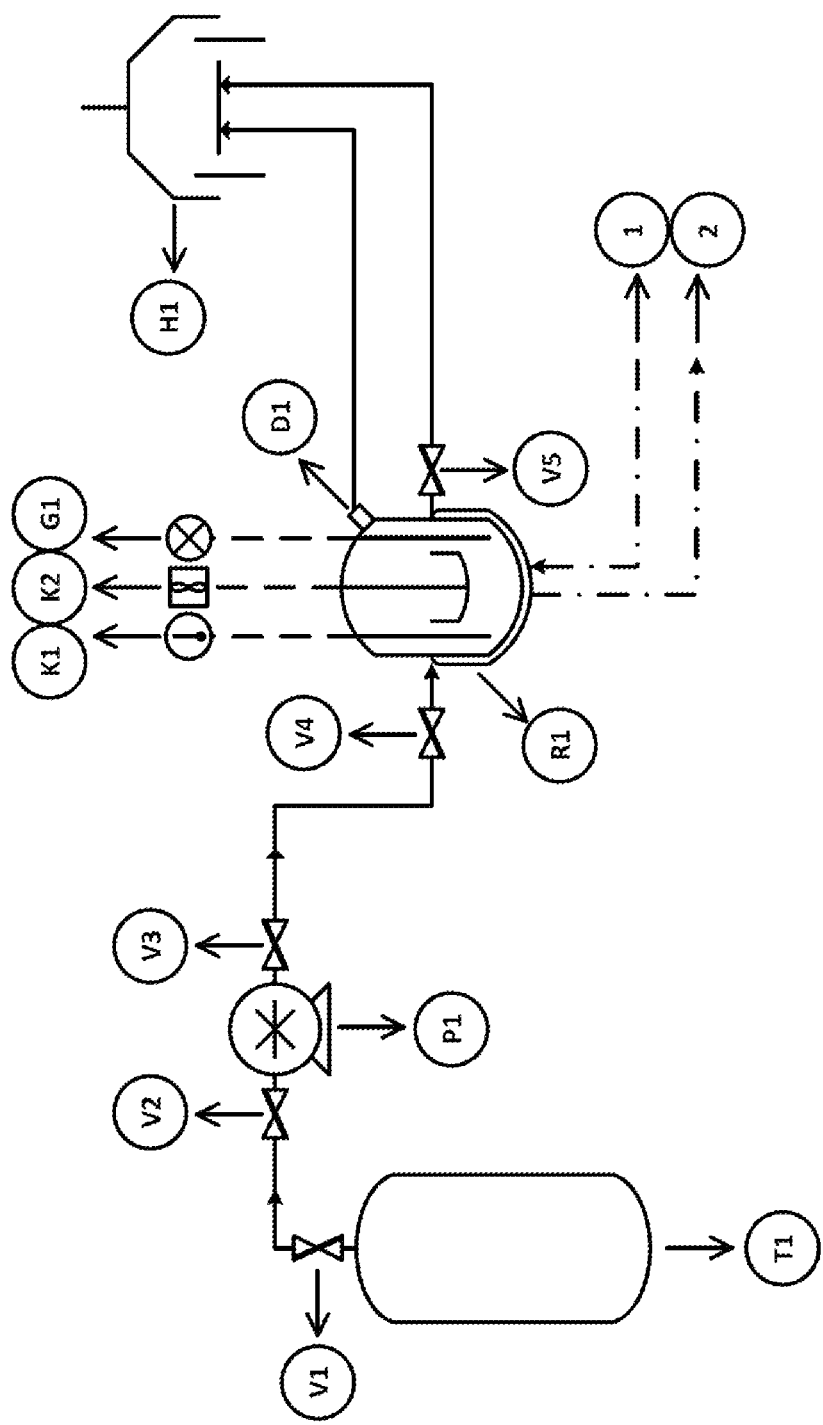
FIG. 1: The Schematic Drawing of Lactide Production from Polylactic Acid with Supercritical or Dense Gas $CO_2$.

A preferred embodiment of the invention is illustrated in FIG. 1. As it can be seen in FIG. 1, the invention comprises a high-pressure, stainless steel reactor (R1), which allows the processing of materials in gas, liquid or solid phase, is coupled with a pressure transducer and display (G1), a rupture disk (D1), a thermocouple and temperature controller (K1), and has inlet (V4) and outlet (V5) valves, a heating jacket, and a mixer (K2). Liquid carbon dioxide is fed to the reactor at the desired flow rate and pressure using a syringe pump (P1).

The main steps of the method for conversion of polylactic acid to lactide in a single stage in supercritical or dense gas carbon dioxide medium comprises the application of the steps below.
 a) filling the high-pressure reactor with $CO_2$,
 b) adjusting the temperature of the reactor to at least 120° C. and/or the pressure to values above the critical pressure (73.8 bar) of carbon dioxide for supercritical conditions, and for dense gas conditions, to pressure less than the critical pressure of carbon dioxide, in the range of 10 bar and 73 bar.
the steps of a and b can be applied at the desired sequence.

Preferably, the heating and pressurization of the reactor are carried out stepwise. This comprises charging of carbon dioxide to the reactor at the temperature and pressure ensuring that the loaded $CO_2$ remains in gas phase, increasing of the reactor temperature to the reaction temperature, and filling the reactor with $CO_2$ to the reaction pressure.

The preferred conditions are such that, the temperature increase should be between 5-10° C. per minute, preferably 10° C. per minute, the reactor temperature should be between 120-390° C., preferably 200° C., and the reactor pressure should be between 74-300 bar for supercritical conditions, preferably at 103 bar, and for the dense gas conditions, between 10-73 bar, and that $CO_2$ is charged to the reactor up to the reaction pressure such that the pressure is increased at a rate between 0.05-0.20 bar per second, and that the reaction time is at least 10 minutes. These conditions can be applied either simultaneously or separately.

In an exemplary application of the invention, first, the desired amount of polylactic acid (1) is placed into the reactor (R1) at room condition. The inlet (V4) and outlet (V5) valves of the reactor (R1) are closed, and the stainless steel, high-pressure line connected to the syringe pump (P1) is connected to the reactor inlet valve (V4). The line between the tank and the syringe pump is filled with liquid carbon dioxide from the liquid carbon dioxide tank (T1). The syringe pump inlet valve (V2) is opened and the syringe pump (P1) is filled. The pressure of the syringe pump (P1) is adjusted to the desired pressure, the syringe pump outlet valve (V3) is opened, and the line between the syringe pump and the reactor is filled with liquid carbon dioxide. The reactor temperature is adjusted to the desired temperature, the reactor inlet valve (V4) is opened, and the reactor is filled with carbon dioxide up to the desired pressure. These temperature and pressure ranges must be 120-390° C., and 74-300 bar for supercritical conditions, and 10-73 bar for dense gas conditions, respectively.

The minimum temperature is the temperature where the reaction starts, and the minimum pressure of supercritical $CO_2$ condition is 74 bar, which is above the critical pressure of $CO_2$, for the dense gas condition, the minimum pressure is the pressure which ensures a $CO_2$ density of 0.01 g/ml; the maximum temperature and pressure are temperature and pressure that can be endured by the reactor.

When the reactor (R1) pressure reaches the pressure of the syringe pump (P1), the filling process is completed and the reactor inlet valve (V4) is closed. This moment is recorded as the starting time of the reaction. The reaction time, which is minimum 10 minutes, depends on the PLA type, its molecular weight, amount, and particle size. At the end of the reaction time, the reactor temperature controller (K1) is turned off and the reactor (R1) is left to cool at room temperature. When the reactor (R1) reaches the room temperature, the reactor outlet valve (V5) is opened for the gas inside the reactor to be discharged into the ventilation system (H1). The reaction gas that comprises high concentrations of carbon dioxide can be collected and separated in order to be reused. The reactor (R1) is opened and lactide (2) which is the reaction product is removed from the reactor (R1).

Figure 2:
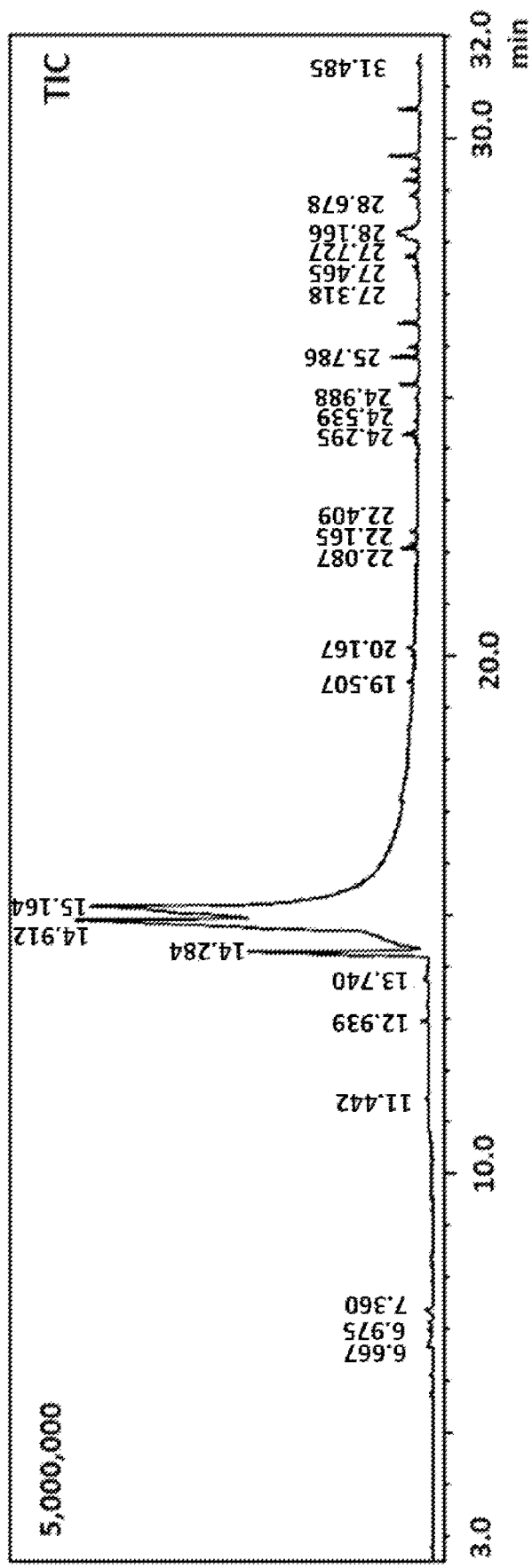
FIG. 2: The GC-MS spectrum of the mixture that is obtained at the end of the reaction.

The gas chromatography-mass spectroscopy (GC-MS) spectrum of the mixture obtained from the reaction performed at 200° C. and 103 bar for 2 hours is given in FIG. 2. As it can be seen in FIG. 2, the lactide isomers that are the main products have been observed at the retention times of 14.2, 14.9, and 15.2 min. High purity (94%) lactide has been obtained from polylactic acid.

In the aforementioned exemplary application, the utilized reactor is a stainless-steel reactor with a heating jacket and a rupture disk, which is resistant to 390° C. and 300 bar.

What is claimed is:

1. A method for a conversion of polylactic acid into lactide in a single step, wherein a reaction is performed in a carbon dioxide medium.

2. The method according to claim 1, wherein the carbon dioxide medium is a supercritical carbon dioxide medium.

3. The method according to claim 1, wherein the carbon dioxide medium is a dense gas carbon dioxide medium.

4. The method according to claim 2, comprising the following steps of:
   a) adjusting a temperature of a reactor to at least 120° C.,
   b) adjusting a reactor pressure to values above a critical pressure of carbon dioxide, wherein the critical pressure is 73.8 bar,
   wherein the steps of a) and b) are applied at a desired sequence.

5. The method according to claim 3, comprising the following steps of:
   a) adjusting a temperature of a reactor to at least 120° C.,
   b) adjusting a reactor pressure to values less than a critical pressure of carbon dioxide, wherein the reactor pressure is in a range of 10 bar to 73 bar,
   wherein the steps of a) and b) are applied at a desired sequence.

6. The method according to claim 1, comprising the following steps of:
   a) carrying out a heating and a pressurization gradually,
   b) filling a reactor with carbon dioxide at a temperature and a pressure ensuring a loaded carbon dioxide remains in a gas phase,
   c) increasing a temperature of the reactor to a reaction temperature,
   d) filling the reactor with the carbon dioxide to a reaction pressure.

7. The method according to claim 1, wherein a reaction time is at least 10 minutes.

8. The method according to claim 2, wherein a reactor pressure is in a range of 74-300 bar, and a maximum pressure does not exceed a pressure endured by a reactor.

9. The method according to claim 3, wherein a reactor pressure is in a range of 10-73 bar, and a maximum pressure does not exceed a critical pressure of carbon dioxide and does not exceed a pressure endured by a reactor.

10. The method according to claim 2, wherein a reactor temperature is in a range of 120-390° C., and a maximum temperature does not exceed a temperature endured by a reactor.

11. The method according to claim 3, wherein a reactor temperature is in a range of 120-390° C., and a maximum temperature does not exceed a temperature endured by a reactor.

12. The method according to claim 2, comprising the following steps of:
   a) carrying out a heating and a pressurization gradually,
   b) filling a reactor with carbon dioxide at a temperature and a pressure ensuring a loaded carbon dioxide remains in a gas phase,
   c) increasing a temperature of the reactor to a reaction temperature,
   d) filling the reactor with the carbon dioxide to a reaction pressure.

13. The method according to claim 3, comprising the following steps of:
   a) carrying out a heating and a pressurization gradually,
   b) filling a reactor with carbon dioxide at a temperature and a pressure ensuring a loaded carbon dioxide remains in a gas phase,
   c) increasing a temperature of the reactor to a reaction temperature,
   d) filling the reactor with the carbon dioxide to a reaction pressure.

* * * * *